United States Patent [19]

Cho

[11] Patent Number: 5,505,692
[45] Date of Patent: Apr. 9, 1996

[54] CONFORMABLE POLYURETHANE CASTING TAPE

[75] Inventor: Edward L. Cho, South Easton, Mass.

[73] Assignee: Johnson & Johnson Professional, Inc., N.J.

[21] Appl. No.: 266,280

[22] Filed: Jun. 27, 1994

[51] Int. Cl.$^6$ ..................................................... A61F 5/00
[52] U.S. Cl. ..................................................... 602/8; 602/6
[58] Field of Search ..................................... 602/1, 5, 6, 8

[56] References Cited

U.S. PATENT DOCUMENTS 3,930,090  12/1975  Campbell, Sr. et al. .............. 428/196
4,668,563  5/1987   Buese et al. ........................... 428/230
4,929,460  5/1990   Lagarde et al. ........................ 426/420
5,256,134  10/1993  Ingham .................................. 602/8

Primary Examiner—Corrine M. Maglione
Assistant Examiner—Michael L. Arness
Attorney, Agent, or Firm—Michael Q. Tatlow

[57] ABSTRACT

A conformable orthopaedic casting tape made with a combination of silicone elastic fiber and a non-elastic fiber is disclosed. The casting tape is capable of stretching 40% to 200% in the length direction and has a power of between 40 and 175 grams per inch width at 30% elongation.

7 Claims, 3 Drawing Sheets

BAR 1    BAR 2    BAR 3

CONFORMABLE POLYURETHANE CASTING TAPE

FIELD OF THE INVENTION

The present invention relates to an improved conformable orthopaedic casting tape. The casting tapes of the present invention provide substantial extensibility and elasticity in both their longitudinal and cross direction which results in improved conformability, and thus allows better application of the casting tapes to the patient and the resulting cast better fits or conforms to the patient's limb.

BACKGROUND OF THE INVENTION

Plaster of Paris casts have been in use to immobilize body members or limbs for some time. The plaster of Paris bandages have been supplemented and, to some extent, superseded by synthetic cast tapes or bandages which employ polymeric materials on a substrate. The preferred polymeric materials are water-cured or water-reactive polyurethane compositions. The polyurethane materials have largely supplanted other polymeric synthetic casting materials. These polyurethane casting materials are of the type which are disclosed in U.S. Pat. Nos. 4,376,438 and 4,411,262.

The fibrous substrate used in the synthetic casting materials is usually a polyester or fiberglass. Although knitted substrates are most common, woven substrates have also been used. The fiberglass materials offer advantages in terms of strength of the finished cast and various constructions of fiberglass fabrics have been used for the substrates for the synthetic casting tapes. The patents mentioned above disclose the use of different fiberglass materials as the substrate for casting tapes. In addition, U.S. Pat. Nos. 3,686,725, 3,787,272 and 3,882,857 disclose specific fiberglass materials, or the treatment of fiberglass yarns, to produce fiberglass substrates which are particularly suitable for use in orthopaedic casts.

U.S. Pat. No. 4,323,061 discloses a cast substrate made from a combination of glass fibers and a second fiber such as cotton, flax, rayon, wool, acrylic resin, nylon, Teflon or polyester. The purpose of the second fiber in the substrate is to hold the curable resin on the substrate.

U.S. Pat. No. 3,332,416 discloses a plaster of Paris cast bandage with a woven substrate made with a combination of elastic and inelastic fibers.

Although fiberglass has been extensively used as a substrate material in orthopaedic casts, with different reactive polymers, all of these casting materials suffer certain disadvantages. One of the major disadvantages is the conformability of the casting tape to the body of the patient. Conformability is the characteristic of the casting tape which has been defined as that property which describes the ability of the bandage or casting tape to adapt to or intimately lay down against the compound curves and protrusions of a body member. Fiberglass casting tapes are generally stiffer than casting tapes made of other fibers, and cast technicians and surgeons have some difficulty conforming the fiberglass tapes to the limbs of a patient.

Casting tapes with improved conformability combine elastic and nonelastic yarns in the tape substrate. U.S. Pat. No. 4,668,563 discloses a polyurethane casting tape made from a high modulus fiber such as fiberglass, polyaramide or polyethlene combined with an elastomeric highly extensible fiber made from natural or synthetic rubber or spandex (polyurethane).

U.S. Pat. No. 5,256,134 discloses a polyurethane casting tape containing an elastic yarn such as natural or synthetic rubber or polyurethane and an inelastic yarn formed from polypropylene, polyester, polyamide, polyethylene or cotton viscose.

A disadvantage of the conformable casting tapes mentioned above is that the elastic fibers employed had serious limitations. As discussed in U.S. Pat. No. 4,668,563, the water reactive polyurethane prepolymer may eventually swell the spandex (polyurethane) filaments causing the filaments to lose their extensibility. This limits the shelf life of conformable casting tapes made with spandex elastic filaments. Natural and synthetic rubber filaments are usually compounded with chemicals which may cause the polyurethane prepolymer to gel prematurely. This may be avoided by treating the rubber filaments with an extraction process or by treating the rubber filaments with an acid. Both of these processes are environmentally detrimental and add cost to the substrate and casting tape.

SUMMARY OF THE INVENTION

The present invention provides a highly conformable polyurethane casting tape made with a substrate containing inelastic and elastic yarns which does not have the instability problems or manufacturing problems of previous highly conformable casting tapes. The casting tapes of the present invention use an elastic yarn made from a silicone elastomer. The silicone elastomeric yarns are chemically inert to polyurethane resins and do not require acid treatment as do natural rubber yarns. The conformable fabric substrate containing the silicone elastomer yarns may be knitted or woven fabric. Knitted fabrics are preferred.

The silicone elastomers used in the yarns of the present invention are high molecular weight linear divinyl polydimethylsiloxanes polymers. These polymers can be efficiently cured using cross-linking agents in the presence of a platinum catalyst or ultraviolet light. Silicone materials that have been found to be useful in the practice of the present invention are available from Wacker Silicones Corporation under the designations Elastosil R401/40, R401/50, R401/60, R401/70, R401/80, R420/30, R420/40, R420/50, R420/60 and R420/70. Mixtures of these materials may also be used. These silicone materials may be cross linked with silicone hydrides in the presence of a platinum catalyst or with sulfur hydrides under U.V. light or without crosslinking agents in the presence of organic peroxides such as 2,4-dichlorobenzoyl peroxide or dibenzoyl peroxide. The silicone elastomers may also contain a reinforcing filler such as amorphous fumed silica. Fibers made from the Elastosil™ silicone materials are commercially available from Patter Products..

DETAILED DESCRIPTION OF THE INVENTION

Figure 1:
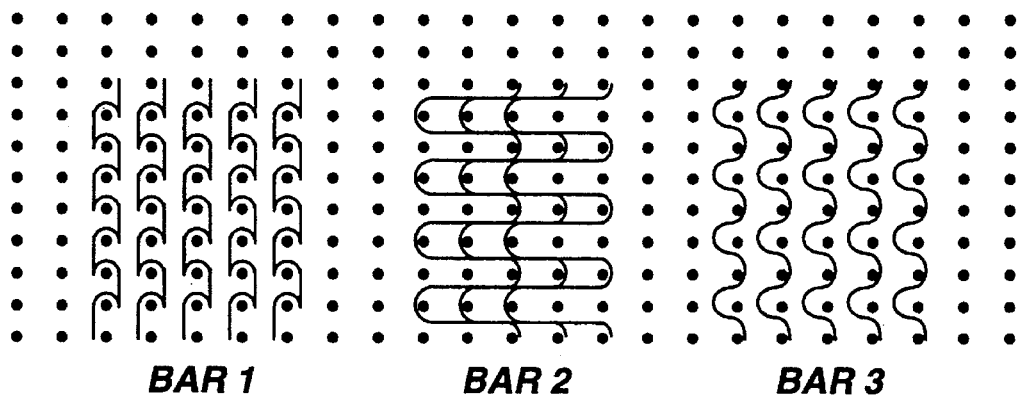
FIG. 1 and 2 are three bar Raschel knit patterns of the type which can be used in the substrate of the present invention in which bar 1 performs a simple chain stitch and bars 2 and 3 perform lapping motions to lay in yarn.

The substrate of the casting tape of the present invention is constructed i.e. woven or knitted, with a combination of continuous filament high tenacity yarns such as fiberglass yarns or lower tenacity yarns such as polyester yarn or combination of fiberglass and polyester yarns and silicone elastomeric yarns. Fiberglass cast substrates are generally characterized as made from filaments which are sized, formed into yarn, and woven or knitted into the desired structure. The cast substrate fabrics of the present invention are knitted or woven fabrics which combine an inelastic fiber such as fiberglass, polyaramide, polypropylene or polyester with a highly elastic silicone fiber. The elastomeric fiber is the silicone fiber described above. In the present invention the knitted substrates are preferably knitted on a Raschel Warp Knitting Machine having 6 to 28 needles per inch. The terms extensible and extensibility used herein refer to the capability of a material, e.g. fiber or fabric, to stretch without breaking. The term elastic refers to the capability of a material, e.g. fiber or fabric, to recover its size and shape after deformation or stretching.

The elastic fiber is present in a woven or knit fabric in the warp or wale yarns, i.e., machine direction, but normally not in the fill yarns. About 0.25 to 35% of the fibers based on the total volume of fibers in the fabric are extensible. The fabric should have a stretch in the longitudinal direction of at least 40% and up to 200% under a static load of 1.5 lb/inch. The fabric knitted or woven with elastic yarns has considerable extensibility in the length direction and it is this lengthwise extensibility that provides greater conformability of the resulting casting tape. The extensibility of the fabric of the present invention is at least 40%, and may be as high as 200%, as determined under a static load of 680 grams per inch of width. This is the extensibility of the fabric coated with the prepolymer. The preferred range of extensibility is between 40 and 120%. In a woven fabric the elastic fiber is also in the warp yarns, and the fabric should have a stretch in the length direction of up to 200% percent.

Knitted fiberglass fabrics previously employed as substrates in casting tapes had some stretchability or extensibility but would not immediately return or recover to their original length after stretching. The present substrate will return substantially to its original length because of the elastomeric fibers in the substrate. The force returning the substrate to its original length causes the substrate to conform to the patient's body.

The elastic fiber component of the substrate can be wrapped or unwrapped yarns. The elastic fiber may be wrapped with cotton, nylon or polyester fiber. The elastic filament may be an extruded filament or it may be a cut thread or filament, i.e. the thread or filament may be cut from a sheet of elastic material. The particular wrapping fiber, if any, is not significant to the present invention. The substrate contains between 65 and 99.75% by volume, of fiberglass or other yarn and between 0.25 and 35% by volume of the elastic yarn. The substrate preferably contains between 1 and 6% by volume of the elastic yarn. The stretch characteristics of the fabrics can be controlled by the selection of the type of yarn, the number of elastic filaments and the size or gauge of the filaments as well as the tension of the elastic yarns during knitting and the knitting pattern of the fabric.

The elastic yarn provides significant stretch or elasticity of the fabric in the length direction. A typical prior art fiberglass cast substrate has stretch in the length direction of from about 5 to 35%. As stated above, the cast substrates of the present invention have a stretch greater than 40% and up to 200% and a preferred stretch of between 60 and 100%. The substrates will also have some stretch in the cross direction which is the result of the knit pattern structure rather than the presence of the elastic yarns. The cross direction stretch is between about 30 and 80%.

The fabric of the present invention has relatively low power. Power is the force necessary to stretch a fabric a given percentage. It is expressed as force per unit width, e.g. grams/inch width for a specific elongation. The power should be low to prevent constriction of the patient's limb after the tape is applied to the patient and before the prepolymer cures. After the prepolymer is cured, the power of the fabric is not a consideration as the cured polymer will prevent any further constriction. The power of the fabric of the present invention is preferably between 40 and 175 grams per inch width to stretch the fabric 30%. The power of any particular knit fabric construction may be adjusted by changing the thickness or gauge of the elastic yarn. The power may also be adjusted by changing the number of elastic yarns in the fabric or changing the knit construction and by changing the tension of the elastic yarns during knitting. The silicone elastic thread employed have been found to be compatible with the water curable polyurethane prepolymer employed in the casting tape.

The elastomer yarns used in the prior art cast substrates were natural rubber or polyurethane, (spandex). The spandex elastic yarns have a tendency to lose their desirable properties when in contact with polyurethane cast prepolymer for extended periods of time, i.e. during product storage. The rubber yarns were treated with acid prior to use to prevent premature hardening of the prepolymer. The use of the silicone elastomers of the present invention avoids these problems.

The silicone elastomers are chemically stable in polyurethane resin, and do not require any wrapping to prevent a direct contact of silicone elastomers with urethane resin. Spandex, for example, has the repeated polyurethane units in a polymer backbone which tend to be miscible in polyurethane resins. This problem can be partially overcome by wrapping the elastomeric yarns with nylon, polyester, or cotton. However, this is not a permanent solution in a conformable polyurethane based casting tapes as the polyurethane resin penetrates the layer of the cover of spandex and eventually attacks the polymer backbone and physical properties may be affected.

The silicone base materials that can be converted to silicone elastic yarns in the present disclosure contain as a major component a silicone of the composition,

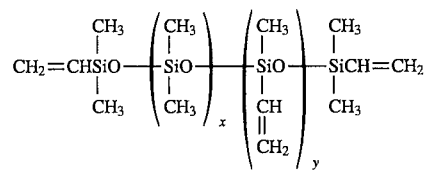

where x is an integer from 30 to 10,000 preferably between 4,000 to 5,000 and y is an integer from 0 to 5,000 preferably between 50 to 200. The molecular weight of the preferred silicone is between 400,000 and 600,000.

The base materials containing the above major chemical component can be crosslinked in many ways. It can be crosslinked with silicone hydride in the presence of a platinum catalyst,

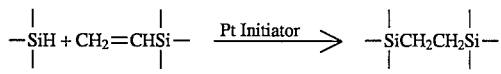

or by a free radical mechanisms in the presence of a peroxide catalyst,

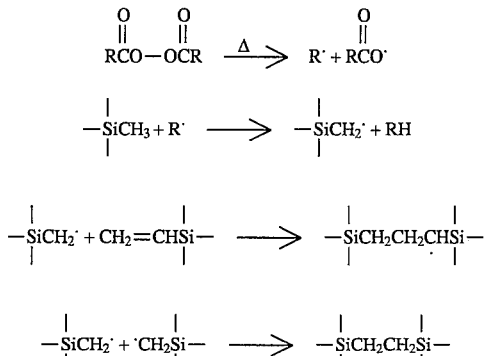

or by ultraviolet light,

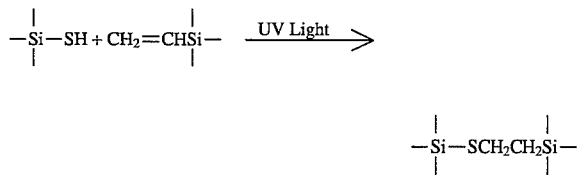

The base silicone materials may be properly compounded prior to the extrusion. In the present art, the base materials are compounded with silicone hydride and a small amount of platinum salt as a catalyst. The composite material is then extruded in the form of continuous fine silicone yarns at ambient temperature, which then undergo heat accelerated crosslinking over the hot air vulcanizer. During this process, the fine silicone strands join side by side together to form a ribbon. The ribbon is further cured on the heated belt conveyer. Heat curing can be accomplished between 300° F. to 900° F., preferably between 400° F. and 600° F. Platinum initiated crosslinking does not generate by-products, provides low shrinkage, needs no post-curing, and requires a very low level of catalyst.

The extruded silicone yarn has a diameter between 5 mil and 15 mil, more preferably between 8 mil and 13 mil for our application to casting tapes. The elongation at break is between 300% to 1500%, more preferably between 600% and 800% for our objective.

The base silicone materials can also be crosslinked in the presence of peroxide initiators such as 2,4-dichlorobenzoyl peroxide and dicumyl peroxide. In this case, no crosslinking agent is required.

Although the free radical initiated crosslinking generates high consistency elastomers, the reaction is only about 85% complete, and an additional post-curing process is required.

Compatibility of silicone elastomers in the polyurethane resin is tested without difficulty. Since the elastomers in the conformable casting tapes are in a stretched form, compatibility of the silicone yarns in polyurethane resin is also evaluated in stretched state and tested in the following manner: silicone yarns are prestretched by 50% and 100%, respectively, and immersed in polyurethane resin in propylene tubes maintained at ambient temperature, 50° C., 70° C., and 90° C., respectively. Samples at 50° C. are kept for 3 months, those at 70° C. for 24 days, and those at 90° C. for 3 days, which all correspond to about 2 years at 20° C. Samples were taken out every week (samples at 90° C. were taken out everyday), cooled to ambient temperature, and stress relaxations were measured. Throughout all measurements, both 50% and 100% prestretched silicone yarns demonstrated an average of 2.77% of stress relaxation per inch of the tested sample. Stress relaxation of 100% prestretched rubber elastomer in polyurethane resin at 70° C. was 7.17% per inch of the sample. Silicone yarns were not attacked by polyurethane resin, and polyurethane resin was not jelled in the presence of silicone elastomers, which suggest that the silicone elastomers are chemically compatible in polyurethane resin.

Because of the chemically stable nature of silicone elastomers and absence of additives in the gumstock which may jell the polyurethane prepolymer prematurely, the silicon elastomers do not require chemical and/or solvent treatments prior to its knitting with in elastomeric yarns. At the same time, the silicone elastomers do not have to be washed with water, which may cause premature jelling of the products if it is not thoroughly dried.

Elastosil™ yarns made from brand silicone provide a significant stretch or elasticity of the fabric in the length direction equivalent to conformable casting substrates in the prior art to conformable substrates in the present invention have a stretch greater than 40% and up to 200%. A preferred stretch of the substrates in the present invention is between 40% and 120% in the length direction. The knit substrates also have some stretch in the cross direction, but this is due to the knit pattern structure, and it is between 30% and 80%.

Numerous knitting patterns may be used in the manufacture of conformable substrates. The substrates are generally knitted using 3 bars in the knitting machine, one of them is for the elastic yarn. It is also possible to make a highly conformable cast substrates by using a two bar fabrics, but such fabrics do not provide an optimum cast strength. When the elastic yarn is in bar 2, or bar 3 in 3-bar knit or in bars 2,3 and or 4 in a 4-bar Raschel knit construction, the tension in the elastic yarn becomes important. The tension in the elastic yarn should be high enough so that gathering or contraction of the fabric occurs to some extent when the fabric is released from the knitting machine. When the fabric is stretched, the gathers are pulled out and further extensibility of the fabric is limited by the non elastic fiber in the chain stitch. The preferred fabric is a 3 bar knit with the elastic silicone yarn in bar 3.

The typical bar patterns for the knit fabric substrates of the present invention are shown in the drawings.

FIG. 1 is a three bar pattern with the elastic silicone thread on the bar 3 and other inelastic yarns on bars 1 and 2.

Figure 2:
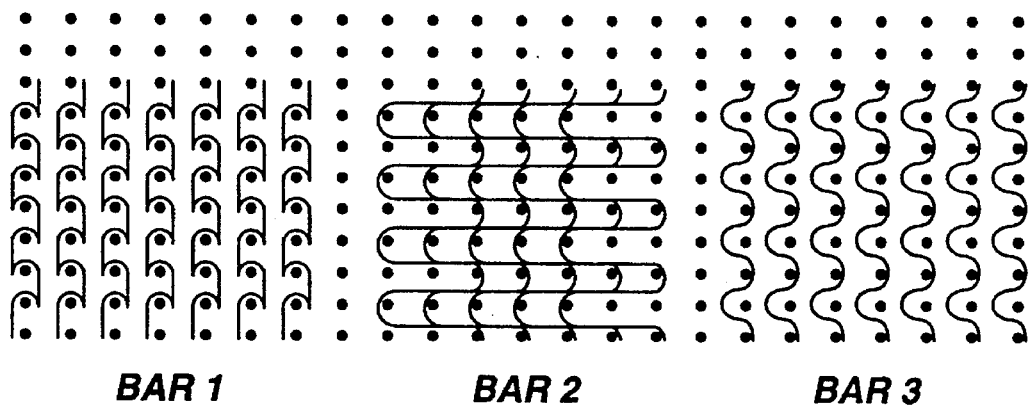

FIG. 2 is a three bar pattern similar to FIG. 1. However, the fabric in FIG. 2 would be heavier as the fill yarns traverse across three needles in FIG. 2 and two needles in FIG. 1. This increases the length of the fill yarn employed and results in greater weight of the fabric.

Also, the patterns of FIGS. 1 and 2 could be modified by employing a zig-zag pattern on bar 3. The particular knit pattern is not critical as long as the fabric has the desired power, lengthwise extensibility and volume of fiberglass or other inelastic fiber in the fabric to produce the desired cast strength. The elastic yarns are preferably laid in a straight pattern to give uniform longitudinal extensibility.

The conformability of casting tapes cannot be objectively measured. However, subjective evaluations of the conformability of synthetic casting tapes based on selective properties have been found to be useful and have good reproduceability between different trained testers. This procedure is explained on page 234 of the Proceedings of the 10th Annual Meeting of the Society for Biomaterials, Apr. 27–May 1, 1984. This procedure, with some modification, can be used to compare the conformability of the present casting tapes. The modifications of the procedure are necessary because of the increased conformability of the casting tapes of the present invention and the fact that the present casting tapes exhibit a property, i.e., the ability of the tape to return or the power of the tape, which is not found to the same extent in prior casting tapes.

Figure 4:
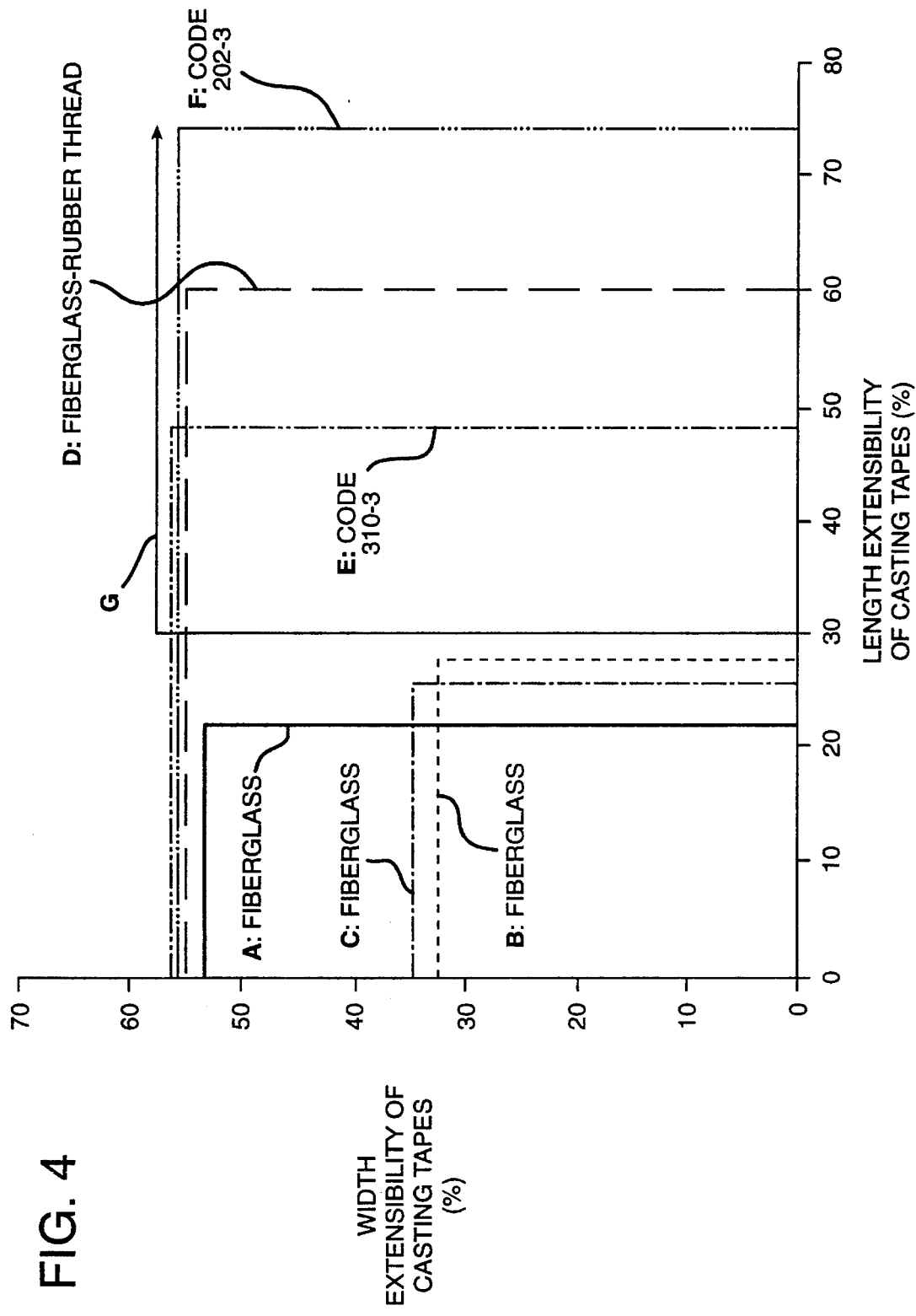
FIG. 4 is a graph comparing the extensibility characteristic of the present casting tape with the casting tapes in the prior art.

The conformability of the present casting tape compared to the conformability of a commercially available polyurethane based fiberglass casting tapes is shown in FIG. 4. The greater the total amount of stretch, i.e., both length and width, the greater the conformability of the tape. The length stretch is determined by suspending a weight of 80 grams per inch of material width from a 10 inch length of tape and measuring the percent of stretch. The same procedure is repeated to determine the percent stretch in the width direction with the material hung from a side rather than its end.

Figure 3:
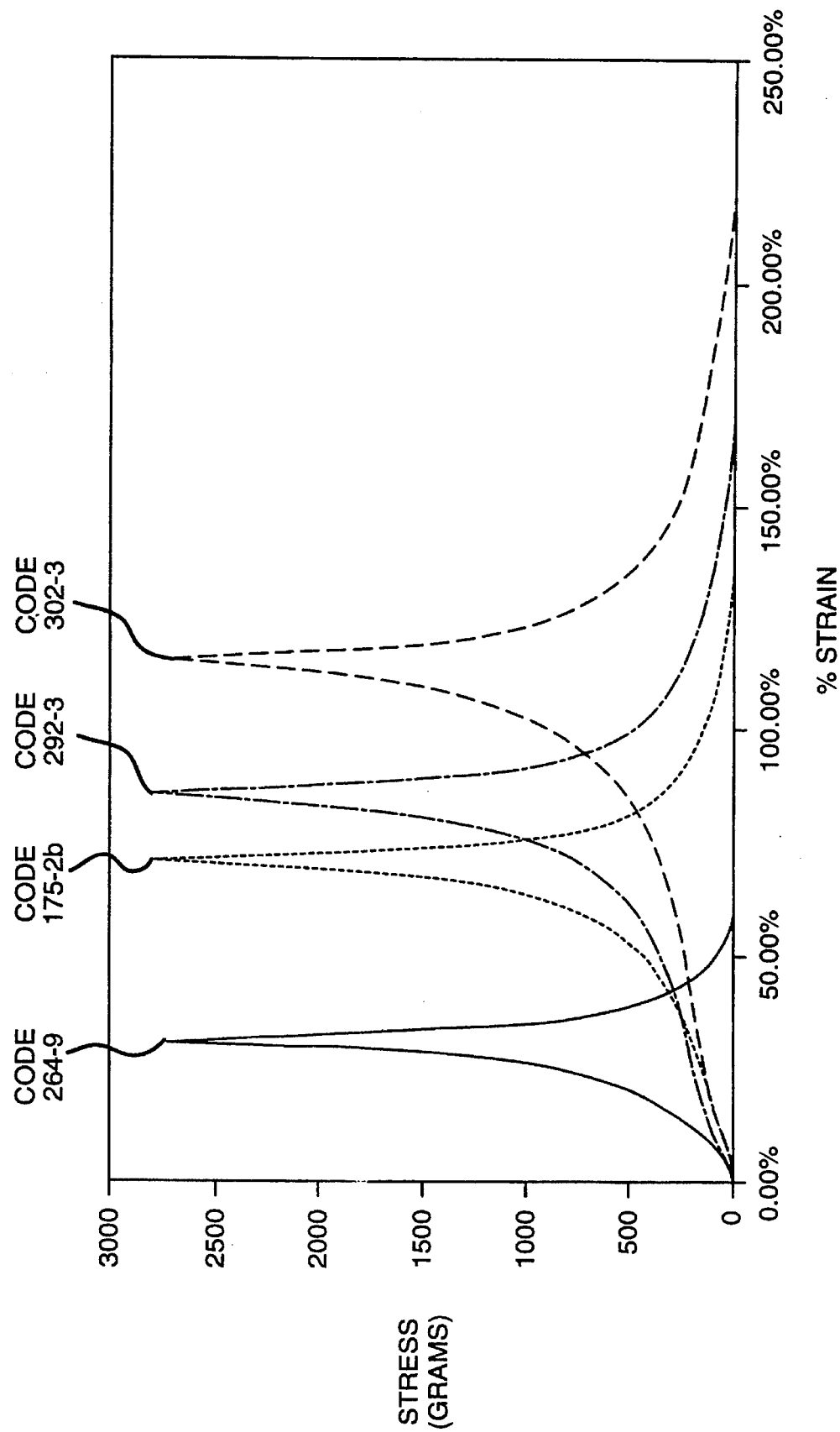
FIG. 3 are extensibility recovery curves of the conformable substrate of the present invention and curves of a commercially available prior art conformable casting tape substrate.

FIG. 3 illustrates the extensibility recovery characteristics of four inch wide fiberglass substrates (Example 2 and Example 1) of the present invention and other commercially available casting substrates having natural rubber threads. The curves in FIG. 3 were generated on Instron Model 1122. The substrate were strained by a force of 1.5 pounds (680 grams) per inch width and then allowed to recover. The downward sloping portion of the curve is the recovery and could be illustrated as returning to the zero point. The curves shown in FIG. 3 are the curves as plotted by the test machine in which the chart paper moves in one direction. The curves show the greater stretch of the substrate fabric of the present invention and the return properties of the fabric. The fabric of the present invention returns faster and also returns to its original length.

In FIG. 4, lines A, B and C show the extensibility of all fiberglass cast bandages. Line D is a fiberglass natural rubber thread cast bandage of the type shown in U.S. Pat. No. 4,668,563. The lines E and F show the extensibilities of conformable bandages of the present invention made with silicone elastomers. Line E shows the conformable bandages with a longitudinal extensibility of 48% and line F in the substrate of Example 1 shows a longitudinal extensibility of 74%.

The stretch of the substrate fabric is determined by securing one end of a sample of fabric, affixing a weight to the other end of the sample. The weight affixed is 80 grams per inch width and the percent stretch is the percent increase in length of the sample of the fabric. Extensibility is a measure of the maximum stretch or extension of the fabric. It is determined in the same manner as stretchability but with a weight of 1.5 pound (680 grams) per inch width of fabric. It should also be noted that the extensibility of the uncoated substrate is more than that of the coated substrate.

The extensibility of the casting tapes may vary depending upon how the substrates are knitted. The stretch of the silicone elastomer can be controlled by the tension between the take away rolls and the input nip rolls of the knitting machine. The number of courses per inch of the substrate change the degree of extensibility of the substrate and the casting tapes. Because of the excellent elasticity of the silicone elastomer, any adjustments for the stretch to provide a given extensibility is accomplished with ease.

Line G in FIG. 4 shows the range of extensibility possible in a casting tape using a silicone elastomer in the elastic yarn.

The following Examples 1–4 show particular substrates that are useful in the present invention.

EXAMPLE 1

A conformable fiberglass substrate (Code-302-3) was knitted on 28 gauge Raschel knitting machine using a 3-bar configuration as in FIG. 1. Bars 1 and 2 contained DE 100 1/0 fiberglass yarns and bar 3 contained 79 gauge Elastosil yarn. The silicone yarn made from Elastosil™ Silicone Elastomer was available from Patter Products under the designation of 1093-1850. Bars 1,2, and 3 had 60, 57, and 40 ends, respectively. The conformable substrate showed the Stretch (80g/in.) of 77.5% and the Extensibility (1.5lb/in.) of 116.3%. The construction of substrate (Code-302-3) had 60 ends in the first bar, 57 ends in the second bar, and 40 ends in the third bar. The chain link numbers were:

Bar 1—2,0,0,2;

Bar 2—0,0,8,8;

EXAMPLE 2

Another conformable fiberglass substrate (Code-292-3) was knitted in the same way as Example 1 using 74 gauge silicone yarn. The substrate had an average of 50% Stretchability (80g/in.) and about 86.3% of Extensibility (1.5lb/in.). The designation of this silicone yarn from Patter Products was 1093-E0098.

EXAMPLE 3

A conformable substrate (Code-310-3) with Stretchability of about 53% and Extensibility of 80% was also constructed with fiberglass yarn and an silicone yarn. Knitting configuration was similar to Example 1, and chain link numbers were:

Bar 1—2,0,0,2;

Bar 2—0,0,8,8;

Bar 3—0,0,2,2;

EXAMPLE 4

A conformable polyester substrate (Code-064-4) was knitted on an 18 gauge Raschel knitting machine using a 3-bar configuration as shown in FIG. 1. Bars 1 and 2 contained 1/150/34 texturized polyester and 1/500/100 high tenacity polyester, respectively. Bar 3 contained 88 gauge Palter Products elastic yarn. Bars 1, 2 and 3 had 43,41 and 43 ends, respectively. The substrate showed an average of 76% stretchability. The extensibility was 86%. The knitting configuration was:

Bar 1—2,0,0,2

Bar 2—0,0,6,6

Bar 3—2,2,0,0

EXAMPLE 5

A sample of the silicone rubber was tested for stability. Ribbons of Elastosil™ silicone elastomer consisting of 50 strands of fiber were prestretched for 50% and 100%, respectively, to simulate the degree of stretch in a substrate, and aged at 90° C. for 3 days. Both samples were cooled to ambient temperature, and the lengths were remeasured. In each case, an average 3% of stress relaxation was observed per inch of sample. In natural rubber, the percent stress relaxation was about 7%.

EXAMPLE 6

Elastosil Ribbons made from Elastosil silicone, one lot with 40 Durometer hardness and one lot with 50 Durometer hardness were prestretched as in Example 5 and immersed in a urethane prepolymer at 90° C. for 3 days. After 3 days, the samples were cooled to ambient temperature, the resin was completely and carefully wiped from the samples in a Dry Box under nitrogen, and the lengths were remeasured. The observed stress relaxation was consistent and was about 3% per inch. The samples were compared with a control sample under the photomicroscope and there was no chemical attack on the fiber by the urethane resin.

EXAMPLE 7

The study described in Example 6 was repeated at 70° C. for 24 days and 50° C. for 3 months. All results were consistent as above, and it demonstrated that the yarns made from Elastosil silicone elastomer were highly compatible in polyurethane resin.

EXAMPLE 8

A conformable fiberglass substrate knitted with silicone Elastosil yarns as described in Example 1 (Code-302-3) was coated with polyurethane prepolymer with approximately 45% of add-on, and aged at 70° C. for 25 days. The bandages maintained its original extensibility of about 74%.

EXAMPLE 9

The conformable substrate (Code-310-3) was also coated with about 45% of polyurethane resin, and the bandage was tested as Example 8. It maintained original extensibility of about 48%.

EXAMPLE 10

CRUSH STRENGTH

Crush strengths of samples of the casting tape was determined as follows:

A cast cylinder is made by wetting a cast tape bandage to be tested and wrapping five layers of the casting tape about a two and one half inch diameter test dowel. Hard pressure is asserted on the layers for 10 seconds to laminate them to one another. The cast cylinder is removed from the test dowel and placed in the jaws of a Chatillion Universal Compressor (Test Strand Model USTM) which is set to close at a deformation speed of twelve inches per minute. The jaws are set to touch the test cylinder and individual cylinders are crushed to a deformation of 1 centimeter at 15 minutes, 1 hour and 24 hours after the tape is wetted. The force necessary to deform the cast is the reported cast strength.

|  | Code-175-2B | Code-302-3 | Code-310-3 |
|---|---|---|---|
| Bandage Width (in.) | 4.03 | 4.00 | 4.13 |
| Set Time (min.) | 4.03 | 3.67 | 3.80 |
| Crush Strength |  |  |  |
| 15 min. (in lb.) | 41.06 | 43.06 | 38.61 |
| 1 hr. (in lb.) | 71.50 | 74.01 | 67.22 |
| 24 hrs. | 114.30 | 125.50 | 108.90 |
| Cylinder weight | 58.54 | 64.53 | 60.97 |

Thus, the crush strength of the conformable bandages containing silicone elastomers are comparable to that of bandages containing the natural rubber.

EXAMPLE 11

A woven substrate was constructed with 81 ends of 2/150/33 heat treated polyester yarns and 40 ends of a silicone elastomeric yarns in the warp and 38 fill yarns of 1/500/96 heat treated polyester in a plain 1/1 weaving pattern. The extensibility of the substrate was 172.5%. The substrate was coated with a typical polyurethane cast resin at an add on level of 60% by weight. The finished tape had an extensibility of 102%. The 24 hour crush strength determined as in Example 10 was 98.7 pounds and the cylinder weight was 59.8 grams.

We claim:

1. An orthopaedic casting tape containing a fibrous substrate impregnated with a water-reactive polyurethane prepolymer, said substrate comprising a combination of an inelastic fiber and a silicone elastomeric fiber which is not substantially reactive with the prepolymer and which will maintain its elastic properties for at least 12 months after impregnation with the prepolymer, the silicone elastomeric fiber being incorporated in the substrate in the length direction of the substrate to give the substrate an extensibility of between 40% and 200% in the length direction, said substrate having a power such that the force necessary to extend the substrate to 30% elongation is between 40 and 175 grams per inch of substrate width, said silicone elastomeric fiber comprising a crosslinked silicone having the composition:

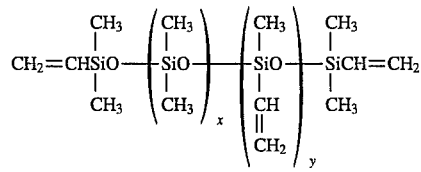

where x is an integer from 4000 to 5000 and y is an integer from 50 to 200 and the silicone composition has a molecular weight between 400,000 and 600,000.

2. The casting tape of claim 1 in which the inelastic fiber comprises 65% to 99.75% by volume of the fiber in the substrate and the silicone elastomeric fiber comprises 0.25% to 35% by volume of the fibers in the substrate.

3. The casting tape of claim 1 in which the substrate has an extensibility in the length direction up to 170% under a static load of 680 grams per inch of width.

4. The casting tape of claim 1 in which the substrate is a Raschel knit fabric and in which the elastomeric fiber is along the length of the fabric.

5. The casting tape of claim 1 in which the inelastic fiber is fiberglass.

6. The casting tape of claim 1 in which the substrate is a 3 bar Raschel knit fabric and the elastomeric fiber is in bar 3 of the substrate.

7. The casting tape of claim 1 in which the inelastic fiber is high tenacity polyester.

* * * * *